United States Patent [19]
Ciganek

[11] 4,077,977
[45] Mar. 7, 1978

[54] ETHENOANTHRACENES

[75] Inventor: Engelbert Ciganek, Kennett Square, Pa.

[73] Assignee: E. I. Du Pont de Nemours and Company, Wilmington, Del.

[21] Appl. No.: 690,591

[22] Filed: May 27, 1976

Related U.S. Application Data

[63] Continuation-in-part of Ser. No. 511,066, Sep. 30, 1974, abandoned, which is a continuation-in-part of Ser. No. 417,807, Nov. 21, 1973, abandoned.

[51] Int. Cl.² .......................................... C07D 209/44
[52] U.S. Cl. ............................ 260/326.1; 260/325 PH
[58] Field of Search ....................................... 260/326.1

[56] References Cited
U.S. PATENT DOCUMENTS 3,123,618   3/1964   Schumann et al. ................. 26/326.1

OTHER PUBLICATIONS

Chem. Abstracts 64:PC 17,513f.

*Primary Examiner*—Ethel G. Love

[57] ABSTRACT

Compounds of the formula:

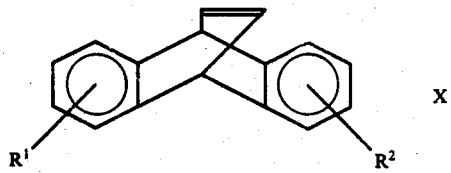

where $R^1$ and $R^2$ are various substituents and X is a bridge having a chain of 3 atoms, including N, are made by internal Diels-Alder reaction of alkynyl-substituted anthracenes. The compounds are useful as inhibitors of free radical vinyl polymerization.

11 Claims, No Drawings

ETHENOANTHRACENES

CROSS-REFERENCE TO RELATED APPLICATIONS

This application is a continuation-in-part of my copending application Serial No. 511,026, filed Sept. 30, 1974, now abandoned, which in turn is a continuation-in-part of my application Serial No. 417,807, filed Nov. 21, 1973, now abandoned.

BACKGROUND OF THE INVENTION

1. Field of the Invention

This invention relates to novel 9,12-bridged ethenoanthracenes containing N in the bridging group, and to methods of making the above compounds.

2. Description of the Prior Art

Unbridged 9,10-ethenoanthracenes are well known in the art, and certain 9,12-bridged ethanoanthracenes have been described (Meek et al., J. Am. Chem. Soc., 74, 761 (1952); ibid, 78, 5413 (1956); ibid, 82, 2566 (1060); Alder and Heimbach, Chem. Ber., 86, 1312 (1953); British Patent 1,266,890). A low yield of a 9,12-bridged ethanoanthracene,

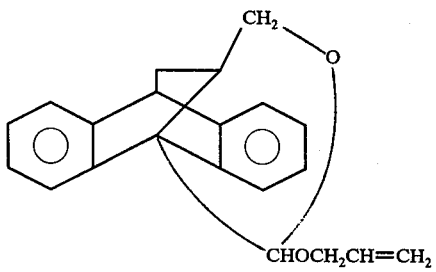

was obtained by an intramolecular Diels-Alder reaction (Meek and Dann, J. Org. Chem., 21, 968 (1956)).

DESCRIPTION OF THE INVENTION

The compounds of this invention have the following structure:

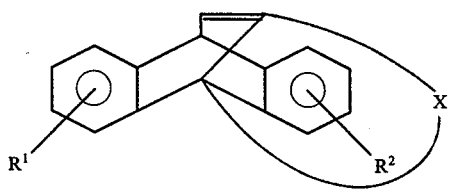

where X is a linear chain of 3 atoms, which contains one central atom of nitrogen, the remaining atoms being carbon substituted with hydrogen, or up to one oxygen to form carbonyl, and where N is substituted with H, alkyl of up to 12 carbon atoms, alkenyl of 3–4 carbon atoms attached to N by a standard carbon atom, cycloalkyl of 3–9 carbon atoms, cycloalkenyl, cycloalkyl lower alkyl, cycloalkenyl lower alkyl, phenyl lower alkyl, adamantylmethyl, benzyl, α-furylmethyl, α-thienylmethyl, or β-phenylethyl. The preferred X linkages are

where $R^3$ is H, alkyl of up to 12 carbon atoms (most preferably a lower alkyl), cycloalkylmethyl of 4–10 carbon atoms or benzyl.

$R^1$ and $R^2$, alike or different, may be hydrogen, lower alkyl, lower perfluoroalkyl, halogen, lower alkoxy, lower alkylthio, lower perfluoroalkylthio, lower acyl, lower alkylsulfonyl, lower perfluoroalkylsulfonyl, di(lower alkyl)aminosulfonyl, sulfamyl, amino, lower alkylamino, and di(lower alkyl)amino, with the proviso that at least one of $R^1$ and $R^2$ be hydrogen. Preferably, $R^1$ and $R^2$ are hydrogen.

The term "lower" as used herein means 1–4 carbon atoms.

Some of the compounds of this invention, e.g. the amines, when heated with an acid catalyst, undergo a rearrangement to dihydromethanodibenzocycloheptapyrroles which, upon reduction, yield tetrahydro derivatives as described in U.S. Ser. No. 448,686 filed Mar. 6, 1974, now abandoned. The amides or lactams of this invention may be rearranged by the action of bromine in a solvent, e.g. methylene chloride, to give dibromodihydromethanodibenzocycloheptapyrrolones. The bromine is then removed and the lactam reduced to give the above-mentioned tetrahydro derivatives. Many of the latter compounds are tranquilizing agents in warm-blooded animals.

All the compounds of the invention are useful as inhibitors of free radical vinyl polymerization.

The 9,12-bridged ethenoanthracenes, I, are numbered as follows:

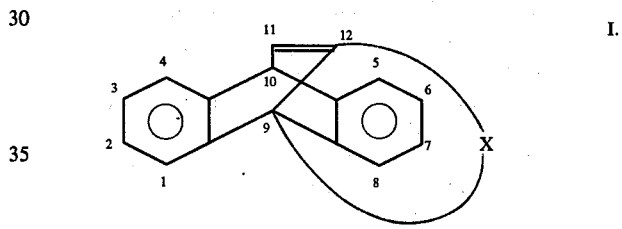

These compounds are prepared by internal Diels-Alder reaction of the corresponding alkynyl-substituted anthracenes as shown by equation (1):

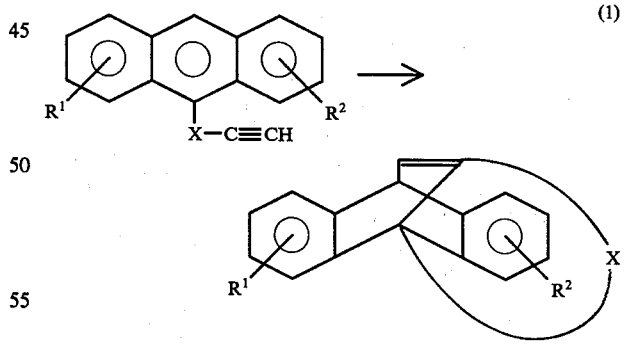

This process can be carried out by heating the alkynylanthracene, either neat or in a suitable inert solvent, preferably an aromatic hydrocarbon, at a temperature of 80–250° C depending upon the particular atoms in the X chain and the values of the substituents R. Reaction is carried out for a sufficient time to effect the cyclization: preferably from 1–48 hours.

The following reactions can be used to make the required alkynyl anthracene compounds used as starting materials.

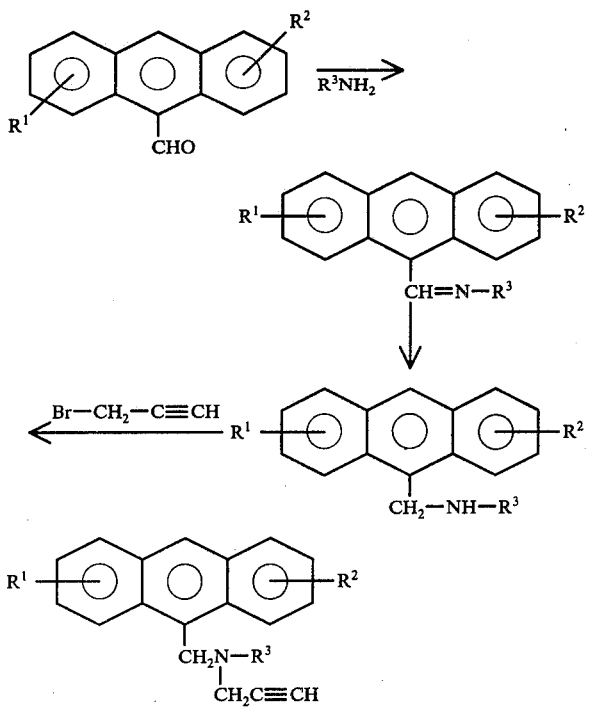

The 9-anthraldehyde compound is reacted with a suitable amine at 25° to 150° C in an alcohol solvent to form an imine. The imine is then reduced with a metal hydride reducing agent such as sodium borohydride or sodium cyanoborohydride in an alcohol such as methanol, ethanol, or isopropanol, which can be the same solvent that is employed to form the imine, at a temperature between 0° C and 100° C.

The resultant secondary amine is then condensed with a propargyl halide, preferably propargyl bromide, in the presence of an inorganic base such as an aqueous solution of an alkali metal carbonate or an organic base which does not react substantially with propargyl bromide, e.g., certain hindered amines including diisopropylethylamine, at a temperature of 0° to 100° C, preferably ambient temperatures.

The alkylnyl substituted anthracenes are then cyclized to compounds of Formula I as described hereinabove.

A procedure to make N-containing compounds of formula I where $R^3$ is H is to react propargylamine with a 9-anthraldehyde in alcohol at 25°–150° C to form the imine. The imine can then be cyclized as described above and thereafter reduced with sodium cyanoborohydride in alcohol solution at 0° to 100° C. Alternatively the reduction can be accomplished prior to cyclization.

The above procedure yields compounds having the formula

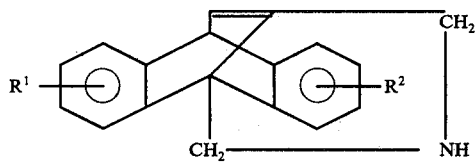

which can be alkylated or acylated to introduce various $R^3$ substituents at the nitrogen atom. Acyl substituents can then be reduced to the corresponding amine.

Yet another method is to react a 9-halomethyl, preferably chloromethylanthracene compound with $R^3NH_2$ in an inert solvent at ambient temperatures to 150° C to form a secondary amine-substituted anthracene which is then reacted with a propargyl halide, preferably bromide, as described above.

Other methods can be employed to make various specific compounds as will be evident from the examples of the specification.

EMBODIMENTS OF THE INVENTION

The following examples illustrate specific embodiments of this invention, but they should not, however, be construed as fully delineating the scope of the discovery.

EXAMPLE 1

3,5-Dihydro-5,9b-o-benzenobenz[e]isoindol-1(2H)-one

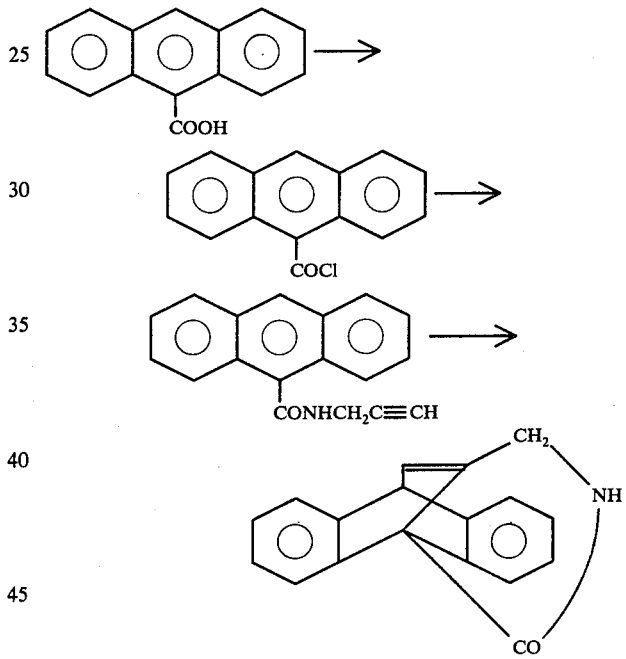

A mixture of 18.85 g of 9-anthroic acid and 60 ml of thionyl chloride is heated under reflux for 1 hour. The excess thionyl chloride is removed under vacuum (30 mm; 90° bath temperature); 50 ml of toluene is added and the mixture is concentrated again. This operation is repeated once more to give 20.6 g of 9-anthroyl chloride as a very moisture-sensitive, yellow solid.

A solution of 13.68 g of 9-anthroyl chloride in 30 ml of tetrahydrofuran is added at 10°–15° to a solution of 10 g of propargylamine in 60 ml of tetrahydrofuran. After stirring at room temperature for 4 hours, the solvent is removed and the residue is stirred with methylene chloride and 5% aqueous sodium bicarbonate solution. The methylene chloride layer is dried and concentrated to give 14.54 g of crude N-propargyl-9-anthramide as a solid. An analytical sample (ethanol) had a melting point of 201°–202°; H nmr spectrum: $\tau$ 1.5–2.8 (m, 9); 3.7 (broad, 1); 5.7 (d of d, 2) and 7.7 ($\tau$, 2.5 Hz, 1).

Anal. Calcd for $C_{18}H_{13}NO$: C, 83.37; H, 5.05; N, 5.40. Found: C, 83.50; H, 5.08, N, 5.29.

A mixture of 10 g of crude N-propargyl-9-anthramide and 200 ml of p-xylene is heated under reflux overnight. The solvent is removed and the residue is sublimed at 200°–210° bath temperature (0.5 micron). Crystallization of the sublimate from 110 ml of acetonitrile gives 4.7 g of 3,5-dihydro-5,9b-o-benzenobenz[e]isoindol-1(2H)-one, mp, 264°–265°, unchanged on recrystallization; nmr spectrum: τ 2.3–3.3 (m, 10); 4.8 (d, J = 6 Hz, 1) and 5.9 (d, J = 2 Hz, 2).

Anal. Calcd for $C_{18}H_{13}NO$: C, 83.37; H, 5.05; N, 5.40. Found: C, 83.19; H, 5.11; N, 5.40.

EXAMPLE 2

2-Methyl-3,5-dihydro-5,9b-o-benzenobenz[e]isoindol-1(2H)-one

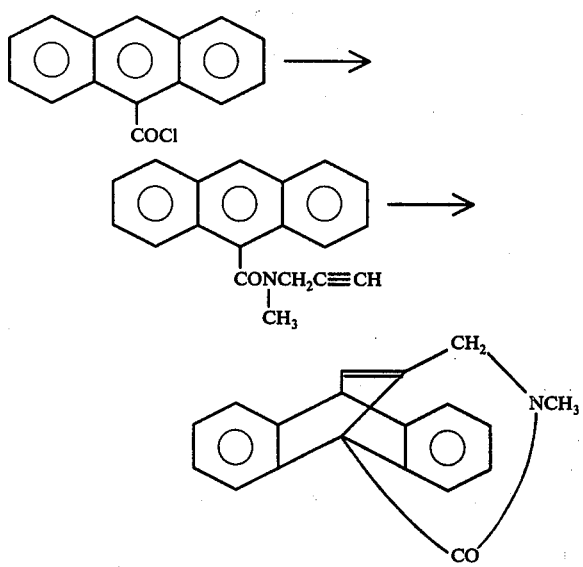

Following the procedure given in Example 1, but using N-methylpropargylamine in place of propargylamine, there is obtained, in turn:

N-methyl-N-propargyl-9-anthramide as an oil; H nmr spectrum: τ 1.7–2.9 (m, 9); 5.4 (d, 2.5 Hz, 1.3); 6.4 (d, 2.5 Hz, 0.7); 6.7 (s, 0.9); 7.4 (s, 2.1); 7.7 (t, 2.5 Hz, 0.7) and 8.0 (t, 0.3). The spectrum shows the presence of two rotamers.

2-Methyl-3,5-dihydro-5,9b-o-benzenobenz[e]isoindol-1(2H)-one, mp, 250°–255°; nmr spectrum: τ 2.3–3.3 (m, 9); 4.8 (d, J = 6 Hz, 1); 5.9 (d, J = 2 Hz, 2) and 6.9 (s, 3).

Anal. Calcd for $C_{19}H_{15}NO$: C, 83.49; H, 5.53; N, 5.13. Found: C, 83.84; H, 5.66; N, 5.10.

EXAMPLE 3

3,5-Dihydro-5,9b-o-benzenobenz[e]isoindole

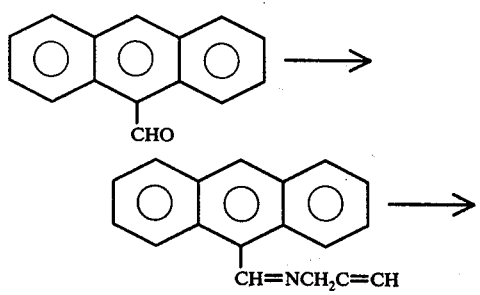

-continued

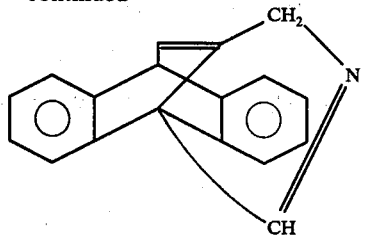

A mixture of 16.7 g of 9-anthraldehyde, 5 g of propargylamine and 100 ml of ethanol is heated under reflux for 1 hour. The solvent is removed and the residue is crystallized from 100 ml of acetonitrile to give 16.1 g (82%) of N-propargyl-9-anthracenemethylenimine; mp, 143°–144°; nmr spectrum: τ 0.2 (t, 2 Hz, 1); 1.7–3.0 (m, 9); 5.1 (t, 2 Hz, 2) and 7.3 (t, 2 Hz, 1).

Anal. Calcd for $C_{18}H_{13}N$: C, 88.86; H, 5.39; N, 5.76. Found: C, 88.83; H, 5.56; N, 5.87.

A mixture of 19.4 g of crude N-propargyl-9-anthracenemethylenimine and 200 ml of p-xylene is heated under reflux for 3 hours. On cooling, 14.6 g of 3,5-dihydro-5,9b-o-benzenobenz[e]isoindole; mp, 212°–214°, precipitates. Another 1.4 g of product is obtained by removing the solvent from the mother liquor and crystallizing the residue from 50 ml of acetonitrile; nmr spectrum: τ 1.1 (m, 1); 2.5–3.5 (m, 9); 4.8 (d, J = 6 Hz, 1) and 5.4 (t, J = 2 Hz, 2).

Anal. Calcd for $C_{18}H_{13}N$: C, 88.86; H, 5.39; N, 5.76. Found: C, 89.10; H, 5.58; N, 5.66.

3,5-Dihydro-5,9b-o-benzenobenz[e]isoindole may also be prepared directly by heating 9-anthraldehyde with propargylamine in p-xylene.

EXAMPLE 4

1,2,3,5-Tetrahydro-5,9b-o-benzenobenz[e]isoindole

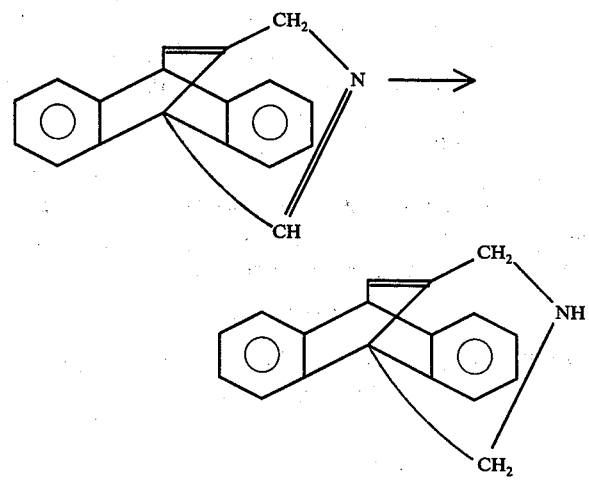

To a slurry of 10.19 g of 3,5-dihydro-5,9b-o-benzenobenz[e]isoindole in 50 ml of methanol and 10 ml of acetic acid is added slowly, with cooling, 4.70 g of sodium cyanoborohydride. The mixture is stirred at room temperature overnight, the excess hydride is destroyed with concentrated hydrochloric acid (ice bath), and the mixture is made basic and extracted with methylene chloride. Removal of the solvent from the dried extract gives 10.49 g of 1,2,3,5-tetrahydro-5,9b-o-benzenobenz[e]isoindole as an oil that slowly solidifies; nmr spectrum: τ 2.6–3.7 (m, 9); 4.9 (d, 6 Hz, 1); 6.0 (s, 2); 6.5

(d, 2 Hz, 2) and 7.5 (s, 1). The hydrochloride melted at 273° (dec) after crystallization from isopropyl alcohol.

EXAMPLE 5

2-Methyl-1,2,3,5-tetrahydro-5,9b-o-benzenobenz[e]-isoindole

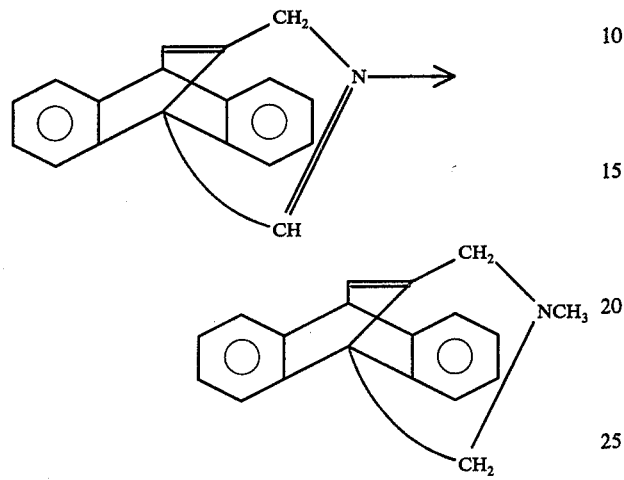

A mixture of 8.19 g of 3,5-dihydro-5,9b-o-benzenobenz[e]isoindole, 25 ml of formic acid and 25 ml of aqueous formaldehyde solution is heated under reflux for 3 hours. Concentrated hydrochloric acid (10 ml) is added, and the volatiles are removed. The residue is stirred with aqueous sodium hydroxide solution and methylene chloride. Removal of the solvent from the dried methylene chloride extracts and crystallization of the residue from acetonitrile gives, in two crops, 5.04 g (58%) of 2-methyl-1,2,3,5-tetrahydro-5,9b-o-benzenobenz[e]isoindole, mp 196°-197°; nmr spectrum: τ 2.4-3.1 (m, 8); 3.3 (d of t, J = 6/2 Hz, 1); 4.8 (d, 6Hz, 1); 6.1 (s, 2); 6.6 (d, 2 Hz, 2) and 7.3 (s, 3).

Anal. Calcd for $C_{19}H_{17}N$: C, 87.99; H, 6.61; N, 5.40. Found: C, 88.05; H, 6.91; N, 5.32.

The N-methyl compound of this example is also obtained by reaction of 1,2,3,5-tetrahydro-5,9b-o-benzenobenz[e]isoindole with formaldehyde and formic acid under similar reaction conditions.

EXAMPLE 6

2-Cyclopentylmethyl-1,2,3,5-tetrahydro-5,9b-o-benzenobenz[e]isoindole

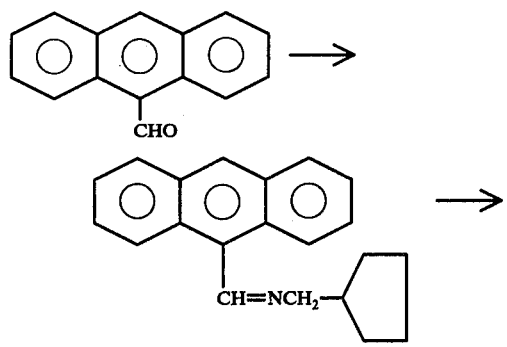

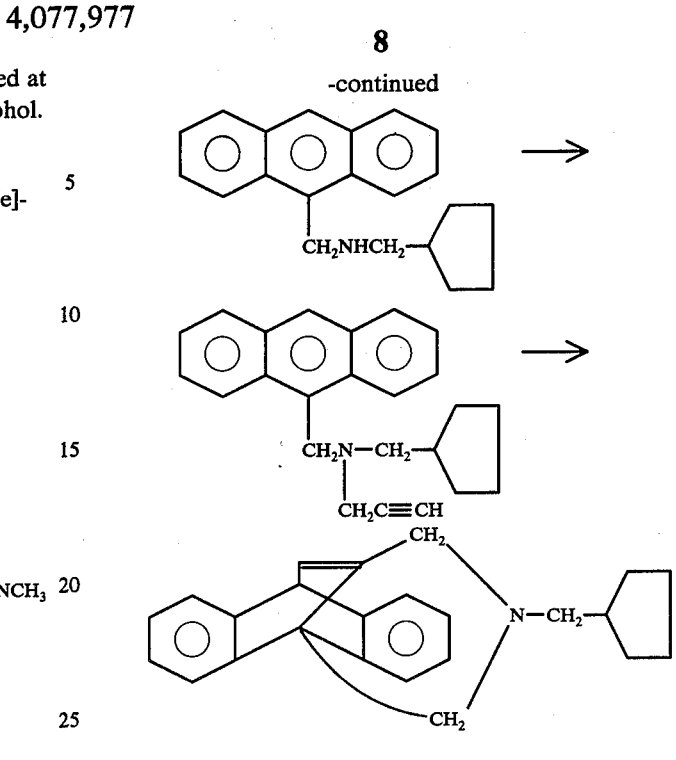

A mixture of 43.5 g of 9-anthraldehyde, 20.97 g of cyclopentylmethylamine and 150 ml of ethanol is heated under reflux for 1.5 hours. The hot solution of N-cyclopentylmethyl-9-anthracenemethyleneimine so obtained is allowed to cool to 60°, and 8.2 g of sodium borohydride is added in small portions, with stirring, while the temperature is maintained at 55-60°. The mixture is then stirred for another 1.5 hours, concentrated hydrochloric acid (35 ml) is added with cooling, and stirring is continued for 0.5 hour. The mixture is then made basic and extracted with methylene chloride. Removal of the solvent from the dried extracts gives 59.1 g of N-cyclopentylmethyl-9-anthracenemethylamine as an oil; nmr spectrum: τ 1.8-3.1 (m, 9); 5.6 (s, 2), 7.5 (d, 7Hz, 2) and 7.8-9.3 (m, 10).

A mixture of 63.5 g of N-cyclopentylmethyl-9-anthracenemethylamine, 50 g of propargyl bromide, 200 ml of methylene chloride and 200 ml of 10% aqueous, potassium carbonate solution is stirred vigorously under nitrogen for two hours. The layers are separated and the aqueous layer is extracted once with methylene chloride. Removal of the solvent from the dried extract gives 63.5 g of N-cyclopentylmethyl-N-propargyl-9-anthracenemethylamine as an oil; nmr spectrum: τ 2.3-3.0 (m, 9); 5.5 (s, 2) 6.8 (d, 2.5Hz, 2); 7.5 (m, 2); 7.7 (t, 2.5Hz, 1) and 7.5-9.2 (m, 9). This product is cyclized by heating under reflux in 200 ml toluene for 1.25 hours. Removal of the solvent and crystallization of the residue from 150 ml of isopropyl alcohol gives 44.4 g of 2-cyclopentylmethyl-1,2,3,5-tetrahydro-5,9b-o-benzenobenz[e]isoindole, identical by infrared and nmr spectroscopy with the sample prepared by acylation of 1,2,3,5-tetrahydro-5,9b-o-benzenobenz[e]isoindole with cyclopentanecarbonyl chloride followed by reduction.

Following this same procedure, but replacing cyclopentylmethylamine with the appropriate amine and substituted 9-anthraldehyde, the following 2-substituted-1,2,3,5-tetrahydro-5,9b-o-benzenobenz[e]isoindoles are prepared:

2-Cyclopropyl-1,2,3,5-tetrahydro-5,9b-o-benzenobenz-[e]isoindole, m.p. 109°-110°; Anal. Calcd. for $C_{21}H_{19}N$; C, 88.38; H, 6.71; N, 4.91. Found: C, 88.21; H, 6.68; N, 5.06.

2-Cyclohexyl-1,2,3,5-tetrahydro-5,9b-o-benzenobenz-[e]isoindole, m.p. 152°–154°; Anal. Calcd. for $C_{24}H_{25}N$: C, 88.03; H, 7.70; N, 4.28. Found: C, 87.82; H, 7.77; N, 4.35.

2-Benzyl-1,2,3,5-tetrahydro-5,9b-o-benzenobenz[e]isoindole, identical by nmr spectroscopy with the sample prepared by benzoylation of 1,2,3,5-tetrahydro-5,9b-o-benzenobenz[e]isoindole followed by reduction.

8-Chloro-2-cyclohexylmethyl-1,2,3,5-tetrahydro-5,9b-o-benzenobenz[e]isoindole; m.p. 144°–146°; Anal. Calcd. for $C_{25}H_{26}ClN$: C, 79.87; H, 6.97; N, 3.73. Found: C, 79.74; H, 7.09; N, 3.66.

EXAMPLE 7

2-Cyclopropylmethyl-1,2,3,5-tetrahydro-5,9b-o-benzenobenz[e]isoindole

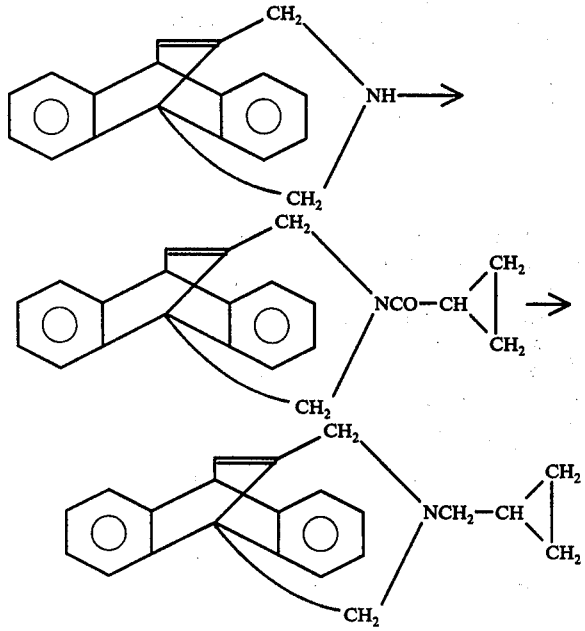

To a slurry of 3.75 g of 1,2,3,5-tetrahydro-5,9b-o-benzenobenz[e]isoindole and 3 g of magnesium oxide in 20 ml of anhydrous tetrahydrofuran is added slowly a solution of 2.4 g of cyclopropanecarbonyl chloride in 5 ml of tetrahydrofuran. After stirring at room temperature for 5 hours, the mixture is filtered and the filtrate is concentrated to dryness. The residue is taken up in methylene chloride, washed with sodium bicarbonate solution, and dried. Removal of the solvent gives 4.07 g of crude 2-cyclopropylcarbonyl-1,2,3,5-tetrahydro-5,9b-o-benzenobenz[e]isoindole which is used in the next step without further purification. A sample crystallized twice from isopropyl alcohol had a mp 171°–173°.

Anal. Calcd for $C_{22}H_{19}NO$: C, 84.31; H, 6.11; N, 4.47. Found: C, 84.41; H, 6.31; N, 4.88.

A mixture of 9.87 g of crude 2-cyclopropylcarbonyl-1,2,3,5-tetrahydro-5,9b-o-benzenobenz[e]isoindole, 4.83 g of lithium aluminum hydride and 100 ml of tetrahydrofuran is heated under reflux for 2 hours. The cooled mixture is treated successively with 4.8 ml of water, 4.8 ml of 15% sodium hydroxide solution, and 14.4 ml of water. Concentration of the filtered mixture gives 9.29 g of crude 2-cyclopropylmethyl-1,2,3,5-tetrahydro-5,9b-o-benzenobenz[e]isoindole, which after one crystallization from isopropyl alcohol melted at 109°–110°. NMR spectrum: τ 2.5–3.5 (m, 9); 4.8 (d, 6 Hz, 1); 6.1 (s, 2); 6.5 (d, 2 Hz, 2); 7.3 (d, 6 Hz, 2) and 8.7–9.8 (m, 5).

Anal. Calcd for $C_{22}H_{21}N$: C, 88.25; H, 7.07; N, 4.68. Found: C, 87.87; H, 7.35; N, 4.70.

Following the procedure of Example 7, but replacing cyclopropanecarbonyl chloride with the appropriate substituted carbonyl chloride, the following 2-substituted 1,2,3,5-tetrahydro-5,9b-o-benzenobenz[e]isoindoles are prepared. All the compounds show the nmr spectral pattern characteristic of the 1,2,3,5-tetrahydro-5,9b-o-benzenobenz[e]isoindole system: τ 2.6–3.2 (m, 8); 3.4–3.5 (d/t, 6/2 Hz, 1); 4.6–5.0 (d, 6Hz, 1) 6.0–6.3 (s, 2) and 6.6–6.8 (d, 2Hz, 2) with minor variations of the chemical shifts depending upon the 2-substituent. The additional signals derived from the 2-substituent are listed separately with each compound.

2-Ethyl-1,2,3,5-tetrahydro-5,9b-o-benzenobenz[e]isoindole; nmr spectrum: τ 7.3 (q, 7Hz, 2); 8.7 (t, 7Hz, 3).

2-Isobutyl-1,2,3,5-tetrahydro-5,9b-o-benzenobenz[e]isoindole; nmr spectrum: τ 7.6 (d, 7Hz, 2); 7.7–8.5 (m, 1); 9.0 (d, 7Hz, 6).

2-Neopentyl-1,2,3,5-tetrahydro-5,9b-o-benzenobenz[e]isoindole; nmr spectrum: τ 7.5 (s, 2); 9.0 (s, 9).

2-Cyclobutylmethyl-1,2,3,5-tetrahydro-5,9b-o-benzenobenz[e]isoindole; nmr spectrum: τ, 7.1–8.5 (m, 9).

2-Cyclopentylmethyl-1,2,3,5-tetrahydro-5,9b-o-benzenobenz[e]isoindole; m.p. 110°–111° C; nmr spectrum: τ 7.3–9.0 (m, 11).

Anal. Calcd. for $C_{24}H_{25}N$: C, 88.03; H, 7.70; N, 4.28. Found: C, 87.68; H, 7.75; N, 4.43.

2-(2-Cyclohexylethyl)-1,2,3,5-tetrahydro-5,9b-o-benzenobenz[e]isoindole; nmr spectrum: τ 7.1–9.5 (m, 15).

2-($\Delta^3$-Cyclohexenylmethyl)-1,2,3,5-tetrahydro-5,9b-o-benzenobenz[w]isoindole; nmr spectrum: τ 4.3 (m, 2); 7.5–9.0 (m, 9).

2-Cycloheptylmethyl-1,2,3,5-tetrahydro-5,9b-o-benzenobenz[e]isoindole; nmr spectrum: τ 7.5–9.2 (m,15).

2-Benzyl-1,2,3,5-tetrahydro-5,9b-o-benzenobenz-[e]isoindole: nmr spectrum: τ 2.4–3.0 (m, 5); 6.3 (s,2).

2-(1-Adamantylmethyl)-1,2,3,5-tetrahydro-5,9b-o-benzenobenz[e]isoindole; nmr spectrum: τ 7.6 (s,2); 7.5–8.5 (m, 15).

2-(2-Phenylethyl)-1,2,3,5-tetrahydro-5,9b-o-benzenobenz[e]isoindole; nmr spectrum: τ 2.6–3.1 (m,5); 7.0 (s,4)

Following the procedure of Example 6, but replacing cyclopentylmethylamine with the appropriate amine and substituted 9-anthraldehyde, the following 2-substituted-1,2,3,5-tetrahydro-5,9b-o-benzenobenz[e]isoindoles were prepared. All the compounds show the nmr spectral pattern characteristic of the 1,2,3,5-tetrahydro-5,9b-o-benzenobenz-[e]isoindole system. Only the nmr signals derived from the 2-substituent are listed.

2-Isopropyl-1,2,3,5-tetrahydro-5,9-o-benzenobenz[e]isoindole; nmr spectrum: τ, 7.6 (septet, J=6Hz, 1H); 9.0 (d, J=6Hz, 3).

2-n-Pentyl-1,2,3,5-tetrahydro-5,9b-o-benzenobenz-[e]isoindole; nmr spectrum: τ, 7.3 (t,2); 8.0–9.3 (m,9).

2-n-Heptyl-1,2,3,5-tetrahydro- 5,9b-o-benzenobenz[e]isoindole; nmr spectrum: τ, 7.4 (t,2); 8.0–9.3 (m,13).

2-(3-Methylbutyl)-1,2,3,5-tetrahydro-5,9b-o-benzenobenz[e]isoindole; nmr spectrum: τ, 7.3 (t, 2); 8.2–8.7 (m,3); 9.1 (d, 6Hz, 6);

2-Allyl-1,2,3,5-tetrahydro-5,9b-o-benzenobenz[e]isoindole; nmr spectrum: τ, 3.7–4.3 (m,1); 4.5–5.0 (m,2); 6.7 (d,2).

2-Cyclobutyl-1,2,3,5-tetrahydro-5,9b-o-benzenobenz-[e]isoindole; nmr spectrum: τ, 6.8-7.2 (m,1); 7.7-8.4 (m,6);

2-Cyclopentyl-1,2,3,5-tetrahydro-5,9b-o-benzenobenz[e]isoindole; nmr spectrum: τ, 7.0-7.5 (m,1); 7.7-8.6 (m,8);

2-(1-Cyclopentylethyl)-1,2,3,5-tetrahydro-5,9b-o-benzenobenz[e]isoindole; nmr spectrum: τ, 7.2-9.2 (m,13);

2-(2-Methylcyclopentylmethyl)-1,2,3,5-tetrahydro-5,9b-o-benzenobenz[e]isoindole; nmr spectrum: τ, 7.3-9.5 (m, 13; mixture of isomers);

2-(3-Methylcyclopentylmethyl)-1,2,3,5-tetrahydro-5,9b-o-benzenobenz[e]isoindole; nmr spectrum: τ, 7.3-9.4 (m, 13; mixture of isomers);

2-(4-Phenylbutyl)-1,2,3,5-tetrahydro-5,9b-o-benzenobenz[e]isoindole; nmr spectrum: τ, 5 additional aromatic H; 7.2-7.6 (m,4); 8.2-8.5 (m, 4);

8-Chloro-2-methyl-1,2,3,5-tetrahydro-5,9b-o-benzenobenz[e]isoindole; nmr spectrum: 7 instead of 8 aromatic protons; 7.5 (s,3).

Following the procedure given in Example 1, but using N-cyclohexylmethylpropargylamine in place of propargylamine, 2-cyclohexylmethyl-3,5-dihydro-5,9b-o-benzenobenz[e]-isoindole-1(2H)-one was obtained; nmr spectrum: τ, 2.4-3.2 (m,8); 3.3 (d/t,1); 4.9 (d,1); 6.0 (d,2); 6.7 (d,2); 8.0-9.3 (m, 11).

Reaction of N-benzyl-9-anthramide with propargyl bromide followed by cyclization gave 2-benzyl-3,5-dihydro-5,9b-o-benzenobenz[e]isoindol-1 (2H)-one; nmr spectrum: τ, ca 2-3.3 (14); 4.8 (d,1); 5.2 (s,2); 6.0 (d, 2).

EXAMPLE 8

2-Cyclohexylmethyl-1,2,3,5-tetrahydro-5,9b-o-benzenobenz-[e]isoindole

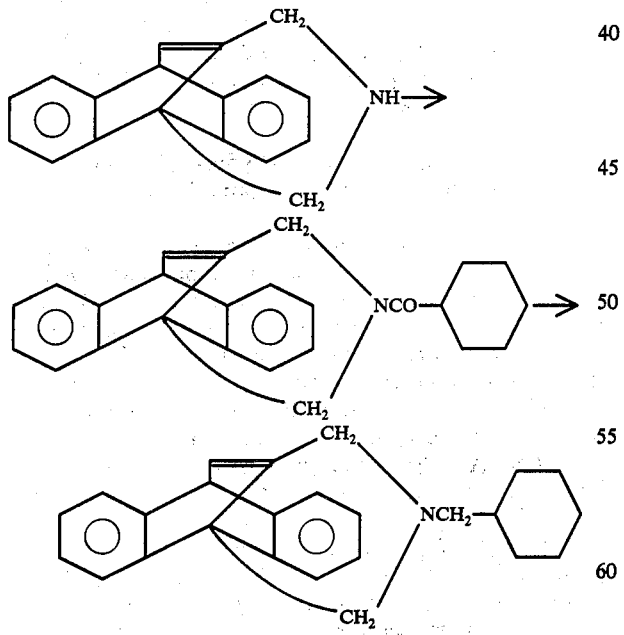

Following the procedure of Example 7, but using cyclohexanecarbonyl chloride in place of cyclopropanecarbonyl chloride, there is obtained in turn:

2-Cyclohexanecarbonyl-1,2,3,5-tetrahydro-5,9b-o-benzenobenz-[e]isoindole, mp 215°-217°.

Anal. Calcd. for $C_{25}H_{25}NO$: C, 84.47; H, 7.09; N, 3.94. Found: C, 84.36; H, 7.05; N, 4.00.

2-Cyclohexylmethyl-1,2,3,5-tetrahydro-5,9b-o-benzenobenz[e]isoindole, mp 157°-158°. NMR spectrum τ 2.5-3.5 (m, 9); 4.9 (d, 2Hz, 2); 7.5 (d, 6Hz, 2) and 7.7-9.5 (m, 11).

Anal. Calcd. for $C_{25}H_{27}N$: C, 87.93; H, 7.97; N, 4.10. Found: C, 87.80; H, 7.66; N, 4.29.

2-Chloro-9-anthraldehyde, reported in the literature, can be employed as starting material according to the general procedures of Examples 3 and 6 to obtain the correspondingly substituted 9.12-bridged ethenoanthracenes (I) as reaction products.

The following substituted 9-anthroic acids, described in the literature, can be employed as starting materials according to the general procedures of Examples 1 and 2 to obtain the correspondingly substituted novel 9,12-bridged ethenoanthracenes (I) as reaction products: 1-chloro-9-anthroic acid, 2-chloro-9-anthroic acid, 2-methyl-9-anthroic acid, 3-chloro-9-anthroic acid.

The compounds of this invention are all useful as polymerization inhibitors for the free radical polymerization of vinyl compounds. This utility is demonstrated with respect to inhibition of the polymerization of acrylonitrile.

EXAMPLE A

In a Carius tube is placed 0.5 ml of distilled acrylonitrile, 2 ml of toluene, 20 mg of azobis(isobutyronitrile) initiator and 70 mg of 2-methyl-3,5-dihydro-5,9b-o-benzenobenz[e]isoindol-1(2H)-one (Example 2). The tube is degassed, sealed under vacuum and shaken at room temperature overnight. No polyacrylonitrile is formed. In a control experiment in which the compound of Example 2 is omitted, solid polyacrylonitrile separates from the solution.

When the following compound is similarly employed as an inhibitor, polymerization of acrylonitrile does not occur:

2-Methyl-1,2,3,5-tetrahydro-5,9b-o-benzenobenz-[e]-isoindole (Example 5).

I claim:
1. A compound of the formula:

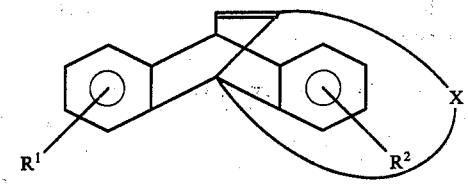

wherein $R^1$ and $R^2$, alike or different, are selected from hydrogen, lower alkyl, lower perfluoroalkyl, halogen, lower alkoxy, lower alkylthio, lower perfluoroalkylthio, acyl of 1-4 carbon atoms, lower alkylsulfonyl, lower perfluoroalkylsulfonyl, di(lower alkyl)aminosulfonyl, sulfamyl, amino, lower alkylamino, and di(lower alkyl)amino; with the proviso that at least one of $R^1$ and $R^2$ is hydrogen; X is a linear chain of 3 atoms, which contains one central atom of nitrogen, the remaining atoms being carbon substituted with hydrogen; where N is substituted with H, alkyl of up to 12 carbon atoms, alkenyl of 3-4 carbon atoms attached to N by a saturated carbon atom, cycloalkyl of 3-9 carbon atoms, cycloalkenyl, cycloalkyl lower alkyl, cycloalkenyl lower alkyl, phenyl lower alkyl, adamantylmethyl, benzyl, α-furylmethyl, α-thienylmethyl, or α-phenylethyl.

2. A compound of claim 1 having the formula:

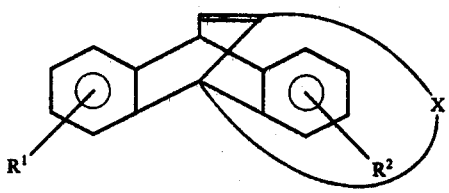

wherein X is —$CH_2$—$NR^3$—$CH_2$— and $R^3$ is H, alkyl of up to 12 carbon atoms, cycloalkylmethyl of 4 to 10 carbon atoms or benzyl.

3. The compound of claim 2 wherein $R^1$ and $R^2$ are each hydrogen.

4. The compound of claim 2 wherein $R^3$ is cycloalkyl methyl of 4 to 10 carbon atoms.

5. The compound of claim 4 wherein $R^3$ is cyclobutyl methyl.

6. The compound of claim 4 wherein $R^3$ is cyclopentyl methyl.

7. The compound of claim 4 wherein $R^3$ is cyclohexyl methyl.

8. The compound of claim 4 wherein $R^3$ is cycloheptyl methyl.

9. The compound of claim 2 wherein $R^3$ is lower alkyl.

10. The compound of claim 3 wherein $R^3$ is cyclopentyl methyl.

11. The compound of claim 2 wherein $R^3$ is hydrogen.

* * * * *